United States Patent

Finel et al.

[11] Patent Number: 5,990,059
[45] Date of Patent: *Nov. 23, 1999

[54] SHAMPOO COMPOSITION

[75] Inventors: Christophe Michel Finel, Compiegne, France; Walter Thomas Gibson; Jonathan David Hague, both of Cheshire, United Kingdom

[73] Assignee: Helene Curtis, Inc., Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/936,102

[22] Filed: Sep. 23, 1997

[30] Foreign Application Priority Data

Sep. 23, 1996 [GB] United Kingdom .................. 9619761

[51] Int. Cl.⁶ .............................. C11D 3/37; C11D 3/22; C11D 1/38
[52] U.S. Cl. .......................... 510/122; 510/121; 510/137; 510/151; 510/466; 424/70.12; 424/70.13; 424/70.22; 134/42
[58] Field of Search .................................. 510/121, 122, 510/137, 151, 466; 424/70.12, 70.22, 70.13; 134/42

[56] References Cited

U.S. PATENT DOCUMENTS

| 4,620,878 | 11/1986 | Gee | 106/287.15 |
|---|---|---|---|
| 4,733,677 | 3/1988 | Gee et al. | 132/7 |
| 4,902,499 | 2/1990 | Bolish, Jr. et al. | 424/70 |
| 5,085,857 | 2/1992 | Reid et al. | 424/70 |
| 5,246,694 | 9/1993 | Birthwistle | 424/70 |
| 5,439,673 | 8/1995 | Murray | 424/70.12 |
| 5,504,149 | 4/1996 | Kosal et al. | 524/837 |
| 5,523,081 | 6/1996 | Edwards et al. | 424/73 |
| 5,578,298 | 11/1996 | Berthiaume et al. | 427/70.122 |
| 5,707,613 | 1/1998 | Hill | 424/78.03 |
| 5,776,444 | 7/1998 | Birtwistle et al. | 424/70.12 |

FOREIGN PATENT DOCUMENTS

| 0268982 | 6/1988 | European Pat. Off. . |
|---|---|---|
| 0432951 | 6/1991 | European Pat. Off. . |
| 0468721 | 1/1992 | European Pat. Off. . |
| 0529883 | 3/1993 | European Pat. Off. . |
| 0674898 | 10/1995 | European Pat. Off. . |

OTHER PUBLICATIONS

International Search Report Application No. PCT/EP 97/05176 mailed Feb., 10, 1998.
Copending application: Serial No. 08/887,998 to Finel et al., filed Jul. 3, 1997, for Hair Styling Composition, assigned to Helene Curtis, Inc. (Not included, for record purposes only).

*Primary Examiner*—Kery Fries
*Attorney, Agent, or Firm*—Mathew Boxer

[57] ABSTRACT

A conditioning shampoo composition for hair and/or skin comprises a stable microemulsion of a high viscosity, slightly cross-linked silicone with a particle size of <0.15 microns, in combination with a deposition polymer and a surfactant.

10 Claims, No Drawings

SHAMPOO COMPOSITION

FIELD OF INVENTION

The invention relates to shampoo compositions, particularly to shampoo compositions which include emulsified particles of silicone, which compositions are mechanically stable and impart good conditioning benefits to hair.

BACKGROUND AND PRIOR ART

The use of silicones in hair treatment compositions is well known and widely documented in the patent literature. Generally, dispersed droplets of silicone are suspended in the composition, which is then applied to the hair to deposit the material on the hair shaft.

Hitherto, steps have had to be taken to prevent the emulsified droplets of silicone oil from agglomerating and the composition creaming during storage. Such steps have for example included the addition of polymers such as Carbopol or certain gums, and/or crystalline materials, to act as suspending agents, but the use of such materials renders the resulting compositions cloudy or opaque, which is a problem if it is desired to formulate optically clear compositions.

The presence of such suspending agents in hair treatment compositions, however, is also disadvantageous because they can lead to dulling of the hair, as well as lowering of other conditioning attributes, as a result of the suspending agent being deposited on the hair in addition to the intended silicone conditioning oil.

It is known in the art that oily cosmetic agents such as silicones can be incorporated into cosmetic compositions by means of microemulsification, whereby the silicone is present as stably emulsified droplets of a particle size of the order of 0.15 microns or less.

For example, U.S. Pat. No. 4 733 677 discloses leave-on hair fixatives containing cationic organic polymer and polydiorganosiloxane microemulsion. EP A 268 982 describes dimethylpolysiloxane microemulsions for various cosmetic uses, the microemulsified dimethylpolysiloxane being formed by emulsion polymerisation and with a particle size of 0.15 microns or less.

In EP A 0 529 883 there is disclosed a hair shampoo comprising a silicone microemulsion in combination with a cationic deposition polymer. This shampoo has good mechanical stability and high optical transparency or translucency since a suspension system is not required to stabilise the microemulsified particles of silicone.

The silicone microemulsion used in EP A 0 529 883 has a particle size of 0.036 microns and a viscosity of 15,000 centistokes. EP A 0 674 898 discloses how the use of higher viscosity microemulsion in such a system improves the conditioning performance. The viscosity of the microemulsion used here is 60,000 centistokes.

A problem is that even the higher viscosity microemulsion disclosed in EP A 0 674 898 does not give a sufficient conditioning benefit for many people.

We have now found that shampoo compositions having excellent mechanical stability and conditioning ability can be obtained by utilising microemulsions of silicone in which the silicone is very slightly cross-linked in the emulsion form. Neither EP A 0 529 883 nor EP A 0 674 898 make any mention of the silicone microemulsion being cross-linked.

DEFINITION OF THE INVENTION

The present invention provides a shampoo composition comprising:

a) from 2–35% of at least one surfactant;
b) 0.01–10% of a microemulsion of particles of a high viscosity slightly cross-linked silicone conditioning polymer having a particle size of <0.15 microns, the emulsion comprising water, emulsifier and the particles;
c) 0.01–10% of a cationic deposition aid.

DETAILED DESCRIPTION OF THE INVENTION

As used herein, the term high viscosity means in excess of 100,000 centistokes. The viscosity preferably ranges between 800,000 and 1.5 million centistokes. Most preferably the viscosity is about 1 million centistokes. The viscosity being measured is the viscosity of the silicone itself and not that of the emulsion or the final shampoo composition. The viscosity is measured in the conventional manner using a rotary viscometer.

As used herein, the term slightly cross-linked means that the percentage of branched monomer units in the silicone conditioning polymer is less than about 0.05%, preferably being in the range about 0.001% to about 0.04%.

At this low level of cross-linking, superior conditioning benefits are observed for the silicone microemulsion. Excellent overall performance has been obtained with silicone microemulsion 0.02% cross-linked.

The microemulsion of cross-linked silicone conditioning polymer is present in compositions of the invention in an amount from about 0.01% to about 10% by weight, preferably 0.3 to 5% by weight based on the total weight of the composition. The lower limit is determined by the minimum level to achieve conditioning and the upper limit by the maximum level to avoid making the hair unacceptably greasy.

Preferred silicone conditioning polymers for use in the invention are polydiorganosiloxanes, preferably derived from suitable combinations of $R_3SiO_{0.5}$ units and $R_2SiO$ units where each R independently represents an alkyl, alkenyl (e.g., vinyl), alkaryl, aralkyl, or aryl (e.g. phenyl) group. R is most preferably methyl.

The preferred silicone conditioning polymers of the invention are slightly cross-linked polydimethyl siloxanes (which have the CTFA designation dimethicone), optionally having end groups such as hydroxyl. Good results have been obtained with dimethicone.

Various methods of making microemulsions of particles of silicones for use in the invention are available and are well known and documented in the art.

One particularly preferred technique for making silicone microemulsions is that described in EP A 228 575.

In that document there is described a method of making a stable microemulsion of high molecular weight silicone polymer and water by sequentially adding at an effective rate a standard emulsion comprising polydiorganosiloxane precursor, surfactant and water to a polymerisation catalyst medium while mixing to form a clear, stable aqueous microemulsion of polydiorganosiloxane.

Another method of making suitable microemulsions for use in the invention are described in EP A 0 138 192.

Cross-linking of the silicone conditioning polymer is typically introduced concurrently during emulsion polymerisation of the polymer through the inclusion of the required amount of trifunctional and tetrafunctional silane monomer units, for example, those of formula $RSi(OH)_3$ wherein R represents an alkyl, alkenyl (e.g. vinyl), alkaryl, aralkyl or aryl (e.g. phenyl) group, preferably methyl.

Suitable microemulsified, slightly cross-linked silicone conditioning polymers are commercially available or can be readily made using conventional techniques well known to those skilled in the art.

Preferably, the average particle size of the silicone material in the microemulsion of the silicone conditioning polymer is less than about 0.05 microns, suitably about 0.045 microns. Such a particle size ensures demonstrable, self suspension of the silicone in the shampoo base, thereby obviating the need for an additional suspension system.

Particle size may be measured by means of a laser light scattering technique, using a 2600D Particle Sizer from Malvern Instruments.

The microemulsion of the silicone is stabilised by a suitable amount of one or more emulsifiers, preferably chosen from anionic, cationic, nonionic, amphoteric and zwitterionic surfactants, and mixtures thereof. The amount of emulsifier will typically be in the ratio of 1:1 to 1:7 parts by weight of the silicone, although larger amounts of emulsifier can be used, eg. 5:1 parts by weight of the silicone or more.

Suitable anionic surfactants are the alkyl sulphates, alkyl ether sulphates, alkaryl sulphonates, alkyl succinates, alkyl sulphosuccinates, acyl taurates, acyl glutamates, N-alkoyl sarcosinates, alkyl phosphates, alkyl ether phosphates, alkyl ether carboxylates, and alpha-olefin sulphonates, especially their sodium, potassium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine and sodium salts of dodecylbenzene sulphonate and sodium N-lauryl sarcosinate. The most preferred anionic surfactants are sodium lauryl ether sulphate 1EO, 2EO, and 3EO, ammonium lauryl sulphate, ammonium lauryl ether sulphate 1EO, 2EO and 3EO, and triethanolamine and sodium salts of dodecylbenzene sulphonate. Sodium lauryl ether sulphate 3EO is preferred as it gives a particularly clear and stable shampoo when used with high viscosity microemulsions.

Suitable cationic surfactants may include quaternary ammonium hydroxides, e.g. teramethylammonium hydroxide, octyltrimethylammonium hydroxide, dodecyltrimethylammonium hydroxide, hexadecyltrimethylammonium hydroxide, octyldimethylbenzylammonium hydroxide, decyldimethylbenxylammonium hydroxide, didodecyldimethylammonium hydroxide, dioctadecyl dimethylammonium hydroxide, tallow trimethylammonium hydroxide, cocotrimethylammonium hydroxide, and the corresponding salts thereof.

Suitable nonionic surfactants may include condensationant products of aliphatic ($C_8$–$C_{18}$) primary or secondary linear or branched chain alcohols or phenols with alkylene oxides, usually ethylene oxide and generally having from 6 to 30 ethylene oxide groups.

Other suitable nonionics include alkylpolyglycosides and mono- or di-alkyl alkanolamides. Examples of the latter nonionics include coco mono- or di-ethanolamide and coco mono-isopropanolamide.

Suitable amphoteric and zwitterionic surfactants may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl and hydroxysultaines, wherein the alkyl and acyl groups gave 8 to 19 carbon atoms. Examples include lauryl amine oxide, cocodimethyl sulphopropyl betaine and preferably lauryl betaine, cocamidoproyl betaine and sodium cocamphopripionate.

A preferred cosmetic composition in accordance with the invention is a shampoo composition which, in addition to the silicone microemulsion comprises further surfactant to provide a deterging benefit. The composition preferably comprises from about 2 to about 35% by weight in total of surfactant. The deterging surfactant is selected from anionic, cationic, nonionic, and amphoteric and zwitterionic surfactants, and mixtures thereof, examples of which are given above. The deterging surfactant may be the same surfactant as the emulsifier.

A further component of shampoo compositions of the invention is a cationic deposition aid, preferably a cationic deposition polymer.

The cationic deposition aid will generally be present at levels of from 0.001 to 5%, preferably from about 0.01 to 1%, more preferably from about 0.02% to about 0.5% by weight. The polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic deposition polymer. Thus when the polymer is not a homopolymer it can contain spacer non-cationic monomer units. Such polymers are described in the CTFA Cosmetic Ingredient Directory, 3rd edition.

Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

The cationic deposition aids can comprise mixtures of monomer units derived from amine- and/or quaternary ammonium-substituted monomer and/or compatible spacer monomers.

Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". ss Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311).

Other cationic deposition aids that can be used include polysaccharide polymers, such as cationic cellulose derivatives and cationic starch derivatives.

Cationic polysaccharide polymer materials suitable for use in compositions of the invention include those of the formula:

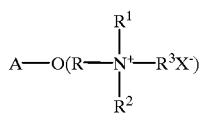

wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion , as previously described.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g.. as described in U.S. Pat. No. 3,962,418, incorporated by reference herein), and copolymers of etherified cellulose and starch (e.g., as described in U.S. Pat. No. 3,958,581, incorporated by reference herein).

Preferably the deposition aid is selected from the group comprising cationic polyacrylamides, hydroxyalkyl cellulose ethers and cationic guar derivatives. Particularly preferred deposition aids are Jaguar C13S with a cationic charge density of 0.8 meq/g. Jaguar C13S is guar hydroxypropyltriamonium chloride. Other particularly suitable materials include Jaguar C15, Jaguar C17 and Jaguar C16 and Jaguar C162, A preferred cellulose ether is Polymer JR400.

The cosmetic compositions of the invention are preferably aqueous based, water forming the basis of the continuous phase of the microemulsion. The compositions preferably comprise water in an amount of from about 20 to about 99% by weight of the total composition.

The compositions of the invention are preferably rinse-off compositions, i.e., suitable for applying to the hair, left thereon for an appropriate period of time and then rinsed off with water.

Compositions in accordance with the present invention may be optically clear.

Depending upon the type of shampoo or silicone employed, one or more additional ingredients conventionally incorporated into shampoo formulations may be included in the compositions of the invention. Such additional ingredients include antibacterial agents, antidandruff agents, foam boosters, perfumes, colouring agents, preservatives, viscosity modifiers, opacifiers, pearlescers, antibacterial agents, antidandruff agents, proteins, polymers, buffering or pH adjusting agents, foam boosters, moisturising agents, herb or other plant extracts and other natural ingredients.

The invention is further illustrated by way of the following non-limiting examples:

EXAMPLE 1

A shampoo composition was prepared by mixing the following components in the amounts stated.

| Component | % by weight |
| --- | --- |
| Sodium lauryl ether sulphate 2EO | 14.0 |
| Cocamidopropyl betaine | 2.0 |
| Jaguar C13S | 0.05 |
| Silicone[1] | 2.4 |
| Preservative, colour, fragrance | q.s. |
| Water | to 100% |

[1]Microemulsified silicone oil containing 0.02% cross-linking, 25% aqueous emulsion, ex Dow Corning.

The silicone has a viscosity of 1 million centistokes and a particle size of 0.045 microns.

In this Example, the % of cross-linking of the silicone refers to the % of branched monomer units in the silicone.

The silicone in this formulation was stable to creaming at 25° C., 37° C. and 45° C. No suspending agent was required for the silicone.

In a dry combing panel test at equivalent levels of silicone deposition, the formulation of Example 1 gave superior dry conditioning benefit to a control formulation in which the silicone (1) was replaced by 60,000 centistokes silicone microemulsion, particle size <0.04 microns, non cross-linked.

We claim:

1. A shampoo composition comprising:
   (a) from 2–35% surfactant;
   (b) from 0.01 to 10% of a microemulsion of particles of a high viscosity, slightly cross-linked silicone conditioning polymer having a particle size of <0.15 microns, wherein said conditioning polymer has about 0.01% to 0.02% branched monomer units and wherein the viscosity of said silicone conditioning polymer has a viscosity of 800,000 to 1.5 million centistokes the emulsion comprising water, emulsifier and the particles and
   (c) 0.01–10% of a cationic deposition aid.

2. A composition according to claim 1, wherein the particles of silicone conditioning polymer have a particle size of <0.05 microns.

3. A composition according to claim 1, wherein the microemulsion (b) is present in the composition in an amount of from 0.3 to 5% by weight.

4. A composition according to claim 1, wherein the cationic deposition aid is a cationic deposition polymer selected from the group consisting of cationic guar derivatives and cationic polyacrylamides.

5. A composition according to claim 1, wherein the surfactant is selected from anionic, cationic, non-ionic, amphoteric and zwitterionic surfactants, and mixtures thereof.

6. A composition according to claim 1 wherein the surfactant is an anionic surfactant.

7. A composition according to claim 6 in which the emulsifier in component (b) is the same anionic surfactant as that used for component (a).

8. A method of conditioning hair and/or skin comprising applying thereto a composition according to claim 1.

9. A composition according to claim 1, wherein said cationic deposition aid has a cationic charge density of between 0.1 meq/g to 4 meq/g.

10. A composition according to claim 1, wherein the cationic deposition aid has a molecular weight between about 5,000 and 10,000,000.

* * * * *